US00PP33171P2

(12) United States Plant Patent
van den Haak

(10) Patent No.: US PP33,171 P2
(45) Date of Patent: Jun. 15, 2021

(54) ***ECHINACEA* PLANT NAMED 'IFECSSRA'**

(50) Latin Name: *Echinacea hybrida*
Varietal Denomination: IFECSSRA

(71) Applicant: Jelle van den Haak, Amsterdam (NL)

(72) Inventor: Jelle van den Haak, Amsterdam (NL)

(73) Assignee: Innoflora Plant Breeding B.V., Heerhugowaard (NL)

( * ) Notice: Subject to any disclaimer, the term of this patent is extended or adjusted under 35 U.S.C. 154(b) by 0 days.

(21) Appl. No.: 16/873,465

(22) Filed: Apr. 17, 2020

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428

CPC ... A01H 5/02; A01H 5/00; A01H 6/14; A01H 6/1448
See application file for complete search history.

(56) References Cited

PUBLICATIONS

Gabot.de Plantarium 2019: novelties part 3, retrieved on Sep. 16, 2020, retrieved from the Internet at https://www.gabot.de/ansicht/plantarium-2019-neuheiten-teil-3-399058.html, 12 pp. (Year: 2019).*

* cited by examiner

*Primary Examiner* — June Hwu
(74) *Attorney, Agent, or Firm* — C. Anne Whealy

(57) ABSTRACT

A new and distinct cultivar of *Echinacea* plant named 'IFECSSRA', characterized by its upright and relatively compact plant habit; moderately vigorous to vigorous growth habit; freely branching habit; strong flowering stems; numerous large single-type inflorescences with three whorls of pink to purplish pink-colored ray florets and reddish brown-colored receptacle spines; and good garden performance.

2 Drawing Sheets

Figure 1:
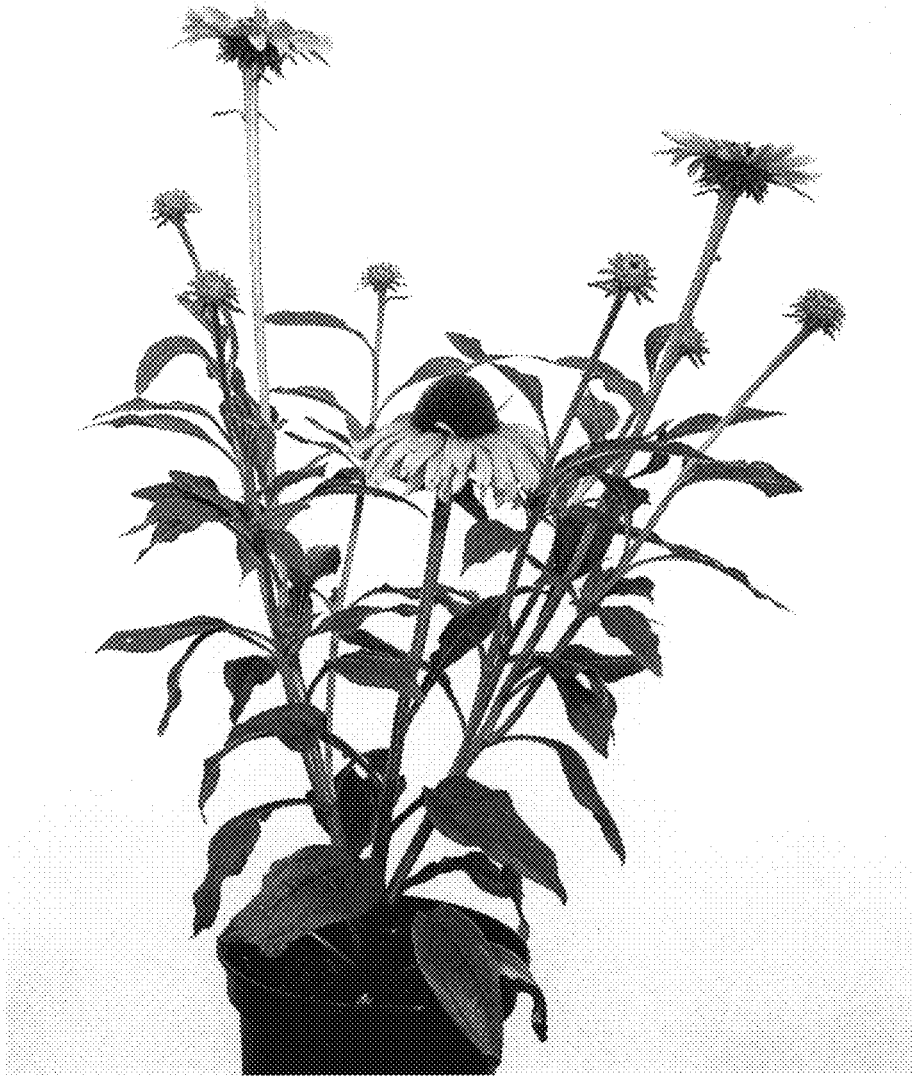

Botanical designation: *Echinacea hybrida.*
Cultivar denomination: 'IFECSSRA'.

STATEMENT REGARDING PRIOR DISCLOSURES BY INVENTOR/APPLICANT

An European Community Plant Breeder's Rights application for the instant plant was filed by the Assignee, Innoflora Plant Breeding B.V. of Heerhugowaard, The Netherlands, on Oct. 29, 2019, application number 2019/2748. Foreign priority is not claimed to this application.

There have been no offers for sale anywhere in the world prior to the effective filing date of this Application and no accessibility to one of ordinary skill in the art.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea hybrida*, and hereinafter referred to by the name 'IFECSSRA'.

The new *Echinacea* plant is a product of a planned breeding program conducted by the Inventor in Heerhugowaard, The Netherlands. The objective of the breeding program is to develop new vigorous *Echinacea* plants with unique and attractive ray floret coloration.

The new *Echinacea* plant originated from an open-pollination in August, 2016 in Heerhugowaard, The Netherlands of a proprietary selection of *Echinacea hybrida* identified as code number 009-15-K012-08, not patented, as the female, or seed, parent with an unknown selection of *Echinacea hybrida* as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in September, 2017.

Asexual reproduction of the new *Echinacea* plant by in vitro meristem culture in a controlled environment in Heerhugowaard, The Netherlands since August, 2018 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSRA'. These characteristics in combination distinguish 'IFECSSRA' as a new and distinct *Echinacea* plant:

1. Upright and relatively compact plant habit.
2. Moderately vigorous to vigorous growth habit.
3. Freely branching habit.
4. Strong flowering stems.
5. Numerous large single-type inflorescences with three whorls of pink to purplish pink-colored ray florets and reddish brown-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Plants of the new *Echinacea* and the female parent selection differ in ray floret color as plants of the new *Echinacea* have pink to purplish pink-colored ray florets whereas plants of the female parent selection have yellow-colored ray florets.

Plants of the new *Echinacea* can be compared to plants of *Echinacea purpurea* 'Summer Cocktail', not patented. In side-by-side comparisons, plants of the new *Echinacea* differ primarily from plants of 'Summer Cocktail' in the following characteristics:

1. Plants of the new *Echinacea* are more compact than plants of 'Summer Cocktail'.
2. Inflorescences of plants of the new *Echinacea* have more ray florets than inflorescences of plants of 'Summer Cocktail'.
3. Plants of the new *Echinacea* and 'Summer Cocktail' differ in ray floret color as plants of the new *Echinacea* have purplish pink-colored ray florets whereas plants of 'Summer Cocktail' have much purplish red-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1 of 2) is a side perspective view of a typical flowering plant of 'IFECSSRA' grown in a container.

Figure 2:
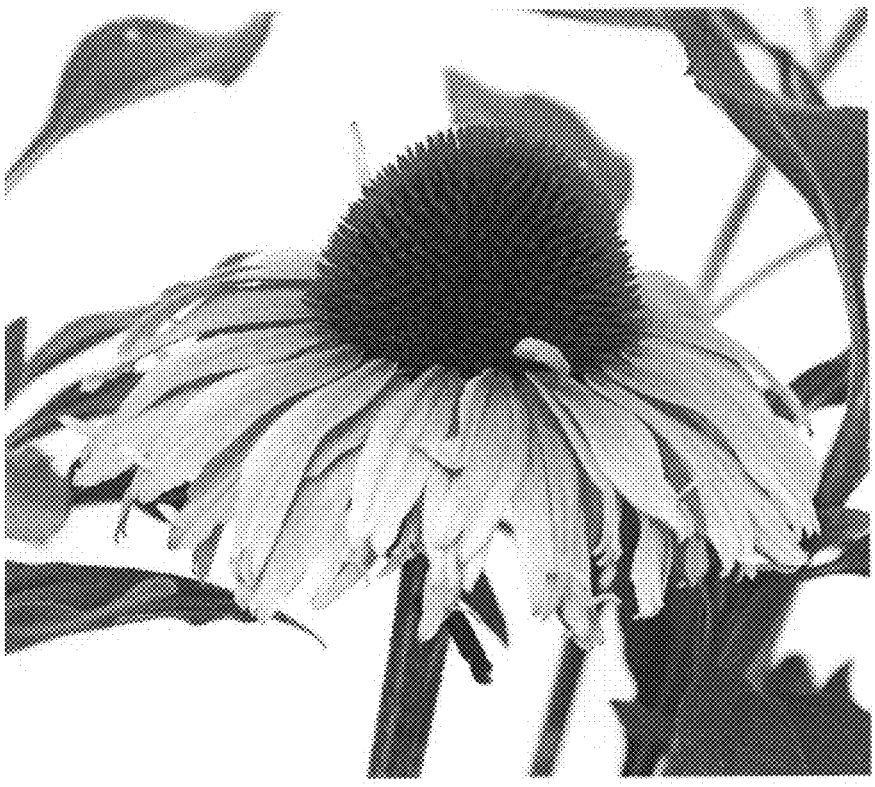

The photograph on the second sheet (FIG. 2 of 2) is a close-up view of a typical inflorescence of 'IFECSSRA'.

DETAILED BOTANICAL DESCRIPTION

The aforementioned photographs and following observations and measurements describe plants grown during the late summer in 17-cm containers in an outdoor nursery in Heerhugowaard, The Netherlands and under cultural practices typically used in commercial *Echinacea* production. During the production of the plants, day temperatures ranged from 10° C. to 25° C. and night temperatures ranged from 4° C. to 15° C. Plants were pinched eight weeks after planting and were 19 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSRA'.

Parentage:

*Female parent.*—Proprietary selection of *Echinacea hybrida* identified as code number 009-15-K012-08, not patented.

*Male parent.*—Unknown selection of *Echinacea hybrida*, not patented.

Propagation:

*Type.*—By in vitro meristem culture.

*Time to initiate roots, summer.*—About twelve days at temperatures about 20° C.

*Time to initiate roots, winter.*—About 16 days at temperatures about 20° C.

*Time to produce a rooted young plant, summer.*—About 36 days at temperatures about 18° C.

*Time to produce a rooted young plant, winter.*—About 42 days at temperatures about 18° C.

*Root description.*—Thick, fleshy; typically white in color, actual color of the roots is dependent on substrate composition, water quality, fertilizer type and formulation, substrate temperature and physiological age of roots.

*Rooting habit.*—Moderately freely branching; sparse.

Plant description:

*Plant form and growth habit.*—Herbaceous perennial; upright and relatively compact plant habit, inverted triangle; freely basal branching habit with about three primary lateral branches each with multiple secondary lateral branches developing per plant; moderately vigorous to vigorous growth habit and moderate growth rate.

*Plant height.*—About 59.2 cm.

*Plant diameter or spread.*—About 35.1 cm.

*Lateral branches.*—Length: About 25.3 cm. Diameter: About 7 mm. Internode length: About 2.9 cm. Aspect: Erect to about 20° from vertical. Strength: Strong. Texture: Densely pubescent; strigose, rough. Color: Close to 143A flushed with close to 144C.

Leaf description:

*Basal leaves.*—Arrangement: Alternate, simple. Length: About 13 cm. Width: About 6.6 cm. Shape: Ovate. Apex: Acute. Base: Attenuate. Margin: Entire; moderately undulate. Texture and luster, upper and lower surfaces: Moderately to densely pubescent, strigose and rough; matte. Venation pattern: Pinnate. Color: Developing leaves, upper surface: Close to 143A. Developing leaves, lower surface: Close to 143B. Fully expanded leaves, upper surface: Close to NN137A; venation, close to N144A. Fully expanded leaves, lower surface: Close to between NN137D and 147B; venation, close to 145B.

*Cauline leaves.*—Arrangement: Alternate, simple. Length: About 8.8 cm. Width: About 3.9 cm. Shape: Ovate to narrowly ovate. Apex: Acute. Base: Attenuate. Margin: Entire; moderately undulate. Texture and luster, upper and lower surfaces: Moderately to densely pubescent, strigose and rough; matte. Venation pattern: Pinnate. Color: Developing leaves, upper surface: Close to 143A. Developing leaves, lower surface: Close to 143B. Fully expanded leaves, upper surface: Close to NN137A; venation, close to N144A. Fully expanded leaves, lower surface: Close to between NN137D and 147B; venation, close to 145B.

*Petioles, basal leaves.*—Length: About 3.8 cm. Diameter: About 2.5 mm by 4 mm. Texture, upper surface: Smooth, glabrous. Texture, lower surface: Mostly glabrous; margins, sparsely pubescent. Color, upper surface: Close to 144A; towards the margins, close to NN137B. Color, lower surface: Close to 144B; towards the margins, close to NN137D.

*Petioles, cauline leaves.*—Length: About 3.7 cm. Diameter: About 2.5 mm by 4 mm. Texture, upper surface: Smooth, glabrous. Texture, lower surface: Mostly glabrous; margins, sparsely pubescent. Color, upper surface: Close to 144A; towards the margins, close to NN137B. Color, lower surface: Close to 144B; towards the margins, close to NN137D.

Inflorescence description:

*Appearance.*—Large single-type inflorescences with ray and disc florets arranged on a capitulum; inflorescences positioned upright above the foliar plane on mostly upright and strong peduncles.

*Flowering habit.*—Freely flowering habit with about twelve developing and fully developed inflorescences per plant.

*Fragrance.*—Faintly fragrant; fragrance is sweet, slightly acidic and pleasant.

*Time to flower.*—Plants flower continuously from early July to late September in The Netherlands.

*Inflorescence longevity.*—Inflorescences maintain good substance for about three weeks on the plant; inflorescences persistent.

*Inflorescence buds.*—Height: About 3.5 cm. Diameter: About 4.2 cm. Shape: Flattened globular. Color: Close to 143A; immature ray florets, slightly lighter than 11D.

*Inflorescence size.*—Diameter: About 12.1 cm. Depth (height): About 6.8 cm. Disc diameter: About 4.7 cm.

*Receptacles.*—Height: About 2 cm. Diameter: About 1.6 cm. Shape: Ovoid. Color: Close to 155A.

*Ray florets.*—Quantity and arrangement: About 60 arranged in about three whorls at the base of the receptacle. Length: About 5.2 cm. Width: About 1.3 cm. Shape: Oblanceolate; carinate. Apex: Praemorse. Base: Cuneate, fused at the base. Margin: Entire. Texture and luster, upper surface: Smooth, glabrous; slightly velvety; matte. Texture and luster, lower surface: Smooth, glabrous; slightly glossy. Aspect: Horizontal to slightly upright, about 10° from horizontal; with development, reflexing downward. Color: When opening, upper surface: Close to 49B. When opening, lower surface: Close to 54C. Fully opened, upper surface: Close to 54B; towards the apex, close to 49B and tinged with close to 151B; venation, similar to lamina; color becoming closer to 49B to 49C tinged with close to 151B with development. Fully opened, lower surface: Close to 55C; towards the apex, close to 151C; venation, similar to lamina; color becoming closer to 55D tinged with close to 151C with development.

*Disc florets.*—Quantity and arrangement: About 600 per inflorescence, arranged spirally at the center of the inflorescence. Length: About 1.2 cm. Diameter: About 2 mm. Shape: Tubular; proximally, 12.5% free, not fused. Apex: Acute. Base: Fused. Margin, free-part: Entire. Texture and luster, inner and outer surfaces: Smooth, glabrous; glossy. Color, when opening, inner and outer surfaces: Apex: Close to 143C. Mid-section and base: Close to 145D. Color, fully opened, inner and outer surfaces: Apex: Close to 143B. Mid-section and base: Close to 144C.

*Receptacle spines.*—Quantity: One per disc floret; about 600 per inflorescence. Shape: Acicular. Apex: Acute. Base: Attenuate. Texture and luster: Smooth, glabrous; glossy. Color: Apex: Close to 175C. Mid-section: Close to 153A. Base: Close to 144A; proximally, close to NN155D.

*Involucral bracts.*—Quantity per inflorescence: About 120 arranged in about four whorls. Length: About 1.2 cm. Width: About 4 mm. Shape: Ovate to narrowly ovate. Apex: Acute. Base: Cuneate. Margin: Entire. Texture, upper surface: Smooth, glabrous; margins, moderately pubescent. Texture, lower surface: Moderately pubescent. Color, upper surface: Close to 137A. Color, lower surface: Close to 137B.

*Peduncles.*—Length: About 20.3 cm. Diameter: About 8 mm. Strength: Strong. Aspect: Upright to about 15° from vertical. Texture: Moderately to densely pubescent; strigose. Color: Close to 143A flushed with close to 144C.

*Reproductive organs.*—Androecium (present on ray and disc florets): Quantity per floret: Five. Filament length: About 5 mm. Filament color: Close to 145D. Anther length: About 4 mm. Anther shape: Lanceolate. Anther color: Close to 200A. Pollen amount: Moderate. Pollen color: Close to 17A. Gynoecium (present only on disc florets): Quantity per floret: One. Pistil length: About 7 mm. Stigma shape: Decurrent, unequal. Stigma color: Close to 200A. Style length: About 5 mm. Style color: Close to 145C. Ovary color: Close to 145D. Seeds and fruits: To date, seed and fruit development have not been observed on plants of the new *Echinacea*.

Pathogen & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'IFECSSRA' as illustrated and described.

* * * * *